United States Patent
Baird, Jr. et al.

(10) Patent No.: US 6,623,626 B2
(45) Date of Patent: Sep. 23, 2003

(54) NAPHTHENE RING OPENING OVER A RING OPENING CATALYST COMBINATION

(75) Inventors: William C. Baird, Jr., Baton Rouge, LA (US); Jingguang G. Chen, Hockessin, DE (US); Gary B. McVicker, Califon, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 09/897,193

(22) Filed: Jul. 2, 2001

(65) Prior Publication Data

US 2002/0038068 A1 Mar. 28, 2002

Related U.S. Application Data

(60) Provisional application No. 60/219,933, filed on Jul. 21, 2000.

(51) Int. Cl.$^7$ .......................... C10G 35/09; B01J 23/40; B01J 23/42; B01J 23/44; B01J 23/46
(52) U.S. Cl. .................. 208/137; 208/138; 208/133; 208/134; 208/15; 502/325; 502/326; 502/327; 502/328; 502/333; 502/334; 502/339
(58) Field of Search .................. 208/15, 133, 134, 208/137, 138; 585/700, 940; 502/325, 326, 327, 328, 333, 334, 339

(56) References Cited

U.S. PATENT DOCUMENTS

| | | | |
|---|---|---|---|
| 3,617,485 A | 11/1971 | Kittrell | 208/59 |
| 3,617,511 A | 11/1971 | Jenkins et al. | 208/112 |
| 3,631,117 A | 12/1971 | Kovach et al. | 260/666 |
| 3,779,897 A | 12/1973 | Wrench et al. | 208/89 |
| 3,943,052 A | 3/1976 | Kmak et al. | 208/140 |
| 3,953,368 A | 4/1976 | Sinfelt | 252/466 |
| 4,018,670 A | 4/1977 | Sinfelt et al. | 208/140 |
| 4,046,673 A | 9/1977 | Paynter et al. | 208/140 |
| 4,134,823 A | 1/1979 | Bertolacini et al. | 208/65 |
| 4,140,626 A | 2/1979 | Bertolacini et al. | 208/216 |
| 4,224,192 A | 9/1980 | Foster et al. | 252/466 B |
| 4,676,885 A * | 6/1987 | Bush | 208/49 |
| 4,723,963 A * | 2/1988 | Taylor | 44/57 |
| 4,783,575 A | 11/1988 | Schmidt et al. | 585/748 |
| 4,834,866 A | 5/1989 | Schmidt | 208/65 |
| 4,956,075 A | 9/1990 | Angevine et al. | 208/120 |
| 5,015,614 A | 5/1991 | Baird, Jr. et al. | 502/250 |
| 5,026,950 A | 6/1991 | Schmidt et al. | 585/737 |
| 5,334,792 A | 8/1994 | Del Rossi et al. | 585/314 |
| 5,345,026 A | 9/1994 | Chang et al. | 585/700 |
| 5,463,155 A | 10/1995 | Galperin et al. | 585/310 |
| 5,763,731 A | 6/1998 | McVicker et al. | 585/737 |
| 5,770,042 A | 6/1998 | Galperin et al. | 208/65 |
| 5,811,624 A | 9/1998 | Hantzer et al. | 585/700 |
| 5,888,922 A | 3/1999 | Galperin | 502/163 |
| 5,906,728 A | 5/1999 | Iaccino et al. | 208/61 |
| 5,925,239 A | 7/1999 | Klein et al. | 208/213 |
| 5,928,498 A | 7/1999 | McVicker et al. | 208/213 |
| 5,935,420 A | 8/1999 | Baird, Jr. et al. | 208/213 |
| 5,993,642 A | 11/1999 | Mohr et al. | 208/46 |
| 6,221,240 B1 | 4/2001 | Klein et al. | 208/213 |

OTHER PUBLICATIONS

Schultz and co–workers (Proc. 5th Intl. Catal. Congr., North–Holland Publ. (Aidam), v.2, 1229–39, (1973)). –No month.

Egan, et al., J. Amer. Chem. Soc., 84, 1204–12 (1962). –No month.

Gault, et al., Adv. Catal., 30, 1–95, (1981). –No month.

Weitkamp, et al., in Structure and Reactivity of Modified Zeolites, Elsevier (Adam), 279–90, (1984)). –No month.

Sergienko, et al., Khim. Geol. Nauk., 2, 65–70 (1976). –No month.

* cited by examiner

Primary Examiner—Nadine G. Norton
(74) Attorney, Agent, or Firm—Gerald J. Hughes; Jeremy J. Kliebert

(57) ABSTRACT

Disclosed is a process for opening naphthenic rings of naphthenic ring-containing compounds, along with catalysts which can be used in that process. The ring opening is accomplished using a ring opening catalyst system which combines an Ir ring opening catalyst with a Pt and Pd catalyst. The combination of the Pt and Pd-containing catalyst with an Ir-containing catalyst incorporates desirable isomerization activity and also results in substantial ring opening activity that enables Ir to be loaded at a level that is substantially below that of Ir-only ring opening processes.

30 Claims, No Drawings

NAPHTHENE RING OPENING OVER A RING OPENING CATALYST COMBINATION

CROSS REFERENCE TO RELATED APPLICATION

This case claims benefit of U.S. Provisional Patent Application Ser. No. 60/219,933 filed Jul. 21, 2000.

FIELD OF THE INVENTION

This invention relates to a method and composition for opening naphthenic rings of naphthenic ring-containing compounds such as distillate. In particular, this invention relates to the use of a catalyst composition comprising a combination of a naphthene ring isomerizing catalyst, preferably containing Pt and/or Pd in an amount effective to isomerize a $C_6$ naphthene ring compound to a $C_5$ naphthene ring compound, and a naphthene ring opening catalyst, preferably containing Ir in an amount effective to ring open naphthene ring compounds.

BACKGROUND OF THE INVENTION

There is an increasing demand for hydrocarbons boiling in the distillate boiling point range ("distillate"). Distillates typically contain paraffins, naphthenes, and aromatics. For fuel quality parameters such as cetane number, gravity and emissions, paraffins are the most desirable components, followed by naphthenes, followed by aromatics. The least desirable are multi-ring aromatic compounds. There is also an increasing demand for paraffinic solvents arising from their low toxicity and biodegradability. Consequently, it is desirable to reduce the cyclic compound content of hydrocarbon solvent blends, in general, and to convert naphthenes to paraffins, in particular. The general process of converting naphthenes to paraffins is referred to herein as ring opening.

Refinery processes that produce distillate fuels often have a limited capability to produce high quality and yields of distillate fuel. For example, conventional hydrogenation processes saturate aromatic rings to form naphthenes, thereby increasing the cetane number and increasing the API gravity (i.e., lowering the density). However, single ring and multi-ring naphthenes have generally lower cetane values and are denser than paraffins having substantially the same number of carbon atoms. The greater density of naphthenes results in reduced volume of the distillate fuel blend relative to compositions containing similar concentrations of paraffins instead of naphthenes. Hydrocracking catalysts, typically composed of hydrogenation metals supported on acidic supports, are also effective for aromatics hydrogenation and for ring opening by cracking. However, cracking tends to make lower boiling point products, including a significant quantity of undesired gas by-products, which lowers the overall boiling range and limits the volume of final distillate product. In fact, hydrocracking products generally do not contain more distillate boiling range paraffins than the hydrocracking feeds. Moreover, a significant portion of the total paraffin concentration in the final product of conventional hydrocracking processes, including gas by-products, are relatively low molecular weight compounds that are outside the distillate boiling range. Thus, the apparent increase in distillate boiling range paraffins and improved distillate fuel quality may result primarily from a combination of the hydrogenation of aromatics and a concentration of paraffins in a reduced volume of distillate product, the latter arising from removing the undesired paraffin gas by-product, i.e., the low boiling point paraffin gas components.

There is therefore a need for selective ring opening processes for converting single and multi-ring aromatic species, including alkyl functionalized derivatives thereof, into distillate boiling range paraffins without producing a significant amount of undesirable low boiling point saturated species. Selectivity for ring opening is related to the propensity for cleavage of a ring bond which results in product molecules having an equivalent number of carbon atoms and at least one less ring than the original molecule, rather than cleavage of a bond which results in a product molecule having fewer carbons than the original molecule. A perfectly selective ring opening process would give only ring bond cleavage to produce molecules having an equivalent number of carbon atoms and at least one less ring than the original molecule. For example, from a hydrocarbon stream containing only single ring naphthenes of n number of carbon atoms, the product from perfect ring opening selectivity would contain only paraffins of n number of carbon atoms. Thus, the greater number of product molecules from a ring opening process having an equivalent number of carbon atoms and at least one less ring than the original molecule, the greater the selectivity for ring opening.

Conventional ring opening processes use a wide range of catalysts, including bifunctional metal hydrogenation-acidic catalysts. However, distillate quality may be improved by controlling paring isomenzations and subsequent dealkylations in order to limit the number of lower cetane, highly branched paraffins that may result from conventional ring opening.

Some conventional processes for forming an improved distillate employ Ir catalysts for opening naphthene ring compounds. Even though distillates such as diesel, jet fuel and heating oil contain at least about 20 vol. %, generally about 20 to about 40 vol. % of $C_6$ naphthenes, the conventional processes open $C_6$ naphthenes at low rates, if at all. This problem is exacerbated with hydrotreated distillates because they have a still greater concentration of $C_6$ naphthenes. In order to overcome this problem of poor opening of $C_6$ naphthene rings, U.S. Pat. No. 5,763,731 teaches using Ir along with at least one acidic co-catalyst, preferably a zeolite, to isomerize the $C_6$ naphthene rings to $C_5$ rings. However, since the resulting $C_5$ ring structure will typically bear increased numbers of substituents, such as alkyl groups, this approach increases the volume of branched paraffins upon ring opening. In addition, the presence of an acidic co-catalyst has a tendency to isomerize any naturally present linear paraffin into a branched paraffin, often resulting in a ring-opened product that has an undesirably high concentration of branched paraffins. Moreover, the process results in increased light saturated gas production, particularly at high temperature.

Another conventional process, set forth in U.S. Pat. No. 5,811,624, uses Ir along with at least certain transition metals for isomerizing $C_6$ naphthene rings to $C_5$ naphthene rings, with the Ir component being particularly effective for opening the $C_5$ naphthene rings. However, the product contains a significant concentration of branched paraffins, which leads to a lower product cetane number.

There is still a need, therefore, for a ring opening process and catalyst which provide a much higher degree of linearity in the ring opened product.

SUMMARY OF THE INVENTION

In one embodiment, a ring opening catalyst system and process of this invention is provided to form a product higher in linear paraffin functionality compared to conventional ring opening catalysts and processes. The process accomplishes this by providing a naphthene ring opening catalyst system comprising a naphthene ring isomerizing catalyst containing a catalytically active naphthene ring isomerization metal supported on a first catalyst support in an amount effective to isomerize a $C_6$ naphthene ring-containing compound to a $C_5$ naphthene ring-containing compound. The catalyst system further comprises a naphthene ring opening catalyst containing a catalytically active naphthene ring opening metal, preferably a Group VIII such as Ir, Pt, Ru, Rh and more preferably Ir, supported on a second catalyst support in an amount effective to ring open a naphthene ring-containing compound.

The isomerizing catalyst and the ring opening catalyst may be mixed together or provided in a stacked bed arrangement. Preferably, the catalytically active isomerization metal is at least one of Pt and Pd. In one embodiment, the isomerizing catalyst contains from about 0.1 to about 2.0 wt. % Pt, Pd, or a combination thereof. Preferably, the ring opening catalyst contains from about 0.01 to about 0.5 wt. % Ir.

In one embodiment, the isomerization and ring opening metals are present at a weight ratio of 50–99 parts of isomerization metal to 50-1 parts of ring opening metal.

The first and second catalyst supports may be independently selected refractory inorganic oxides. Preferably, the refractory inorganic oxides are selected from the group consisting of alumina, silica, zirconia, titania, cluomia, zinc oxide, magnesia, thoria, boria, silica-alumina, silica-magnesia, chromia-alumina, alumina-boria, silica-zirconia, and combinations thereof. More preferably, the first substrate is alumina. Catalyst supports are also referred to herein as substrates.

In another preferred embodiment, either the naphthene ring isomerizing catalyst or the naphthene ring opening catalyst further comprise a hydrogenolysis suppressor selected from the group consisting of Group IB, IIB and IVA metals in an amount effective to moderate cracking of a naphthene ring-containing feed to form methane. Preferably, the hydrogenolysis suppressor is at least one of Cu, Ag, Au, Zn, and Sn. More preferably, the hydrogenolysis suppressor is Sn.

In yet another embodiment, the ring opening catalyst is supported on a modified refractory support having an effective amount of modifier for enhancing selectivity to linear paraffin functionality. Preferably, the modifier is at least one of Cs, Mg, Ca, and Ba. More preferably, the modifier is at least one of Ca, Mg, and Ba. Most preferably, the modifier is Mg.

In still another embodiment, the naphthene ring opening catalyst contains Ir and further contains at least one other Group VIII metal selected from Pt, Ru, and Rh. The Ir and the other, or "second", Group VIII metal are present in an amount effective for opening a naphthene ring at a tertiary carbon site. Desirably, Ir is present in a range of about 0.1 to about 2.0 wt. %, preferably in a range of about 0.3 to about 1.5 wt. %, more preferably in a range of about 0.5 to about 1.2 wt. %, and most preferably in a range of about 0.5 to about 1.0 wt. %, based on the weight of the ring opening catalyst. It is also desirable that the second Group VIII metal be present in a range of about 0.001 to about 2.0 wt. %, preferably in a range of about 0.005 to about 1.5 wt. %, more preferably in a range of about 0.007 to about 1.3 wt. %, and most preferably in a range of about 0.01 to about 1.0 wt. %, based on the weight of the ring opening catalyst.

In another embodiment, there is provided a process for opening naphthene rings of naphthene ring-containing compounds in a feed stream. The process comprises providing a naphthene ring-containing feed stream; and contacting the naphthene ring-containing feed stream with the naphthene ring opening catalyst system of the invention.

Ring opening may be carried out at a temperature ranging from about 150° C. to about 400° C.; a pressure ranging from about 100 to about 3,000 psig; a liquid hourly space velocity ranging from about 0.1 to about 10 V/V/Hr; and a hydrogen treat gas rate ranging from about 200 to about 10,000 standard cubic feet per barrel (SCF/B).

In another preferred embodiment, the feed stream is a petroleum feed stream which has a boiling point of from about 175° C. to about 600° C. For naphthenic rings containing at least one tertiary carbon site, the ring opening process desirably ring opens the naphthene ring at the tertiary carbon site, thereby forming a ring opened product having increased linear paraffin functionality relative to that of the feed stream. The ring opened product may be recovered and may be used "as is" and in blended form. Preferably, the ring opened product is blended with a petroleum stream having a boiling point of about 175° C. to about 600° C., wherein the blend has a cetane number of at least about 40. The petroleum stream may be, for example, one or more of diesel fuel, jet fuel, heating oil, vacuum gas oil, and light cycle oil.

Desirably, the naphthene ring-containing feed stream has a sulfur content of less than about 10 ppm, preferably less than about 1 ppm, more preferably less than about 0.1 ppm. It is also desirable that the naphthene ring-containing feed stream contains less than about 20 wt. % total aromatic compounds.

Also included as part of this invention are the products made by the stated processes.

DETAILED DESCRIPTION OF THE INVENTION

The invention is based in part on the discovery that a catalyst containing at least one of Pt and Pd may be used to isomerize $C_6$ naphthenes to $C_5$ naphthenes and that such an isomerization catalyst may be used in combination with a ring opening catalyst containing at least one Group VIII metal to open the $C_5$ naphthene at a tertiary carbon site. The resulting product therefore contains more linear and less branched hydrocarbon than the products of the conventional processes. Moreover, as acidic co-catalyst is not required, isomerization of linear paraffins in the product to branched paraffins is abated.

Paraffin content of hydrocarbons such as diesel, jet fuel, and heating oil, as well as light cycle oil, compositions may therefore be increased in the practice of the invention in order to increase cetane number. Ring opening of the naphthenes in the hydrocarbon results in a product having a higher degree of linear paraffin functionality in order to provide a fuel having a higher cetane number than the initial hydrocarbon.

As defined herein, compounds having a high degree of linear paraffin functionality have fewer paraffin (i.e., alkyl) side chains and longer paraffin substituents. According to this definition, linear paraffins, particularly $C_{10}$–$C_{20}$ linear paraffins, are the most highly desirable compounds for use as a diesel or jet fuel product, though other compounds having a relatively high degree of linear paraffin functionality are also acceptable. For example, a cycloalkane ring compound having a single, linear alkyl side chain has relatively high paraffin functionality compared to a cycloalkane ring having multiple side chains. By the same definition, an aromatic ring compound having a single, linear alkyl side chain has a relatively high linear paraffin functionality compared to an aromatic ring compound having multiple side chains.

In one embodiment, the naphthene ring opening catalyst system comprises a naphthene ring isomerizing catalyst containing a catalytically active naphthene ring isomerization metal supported on a first catalyst support in an amount effective to isomerize a $C_6$ naphthene ring-containing compound to a $C_5$ naphthene ring-containing compound. The catalytically active naphthene ring isomerization metal is preferably one or more of Pt and Pd. The preferred Pt, Pd, and Pd—Pt-containing catalyst has high selectivity for isomerizing $C_6$ to $C_5$ naphthene rings, and a low selectivity for isomerizing linear paraffin chains to branched paraffin chains.

The catalyst system further comprises a naphthene ring opening catalyst containing a catalytically active naphthene ring opening metal supported on a second catalyst support in an amount effective to ring open a naphthene ring-containing compound. The catalytically active naphthene ring opening metal is preferably Ir. The Ir-containing catalyst has a particularly high selectivity for ring opening $C_5$ naphthene rings, and the combination of the Pt, Pd, and Pd—Pt-containing catalyst and the Ir-containing catalyst results in substantial ring opening activity.

The catalyst system of this invention allows product to be formed which has a high degree of linear paraffin functionality. Moreover, Ir may be employed in an amount that is substantially less than that of Ir-only ring opening catalysts.

The naphthene ring isomerizing catalyst and the naphthene ring opening catalyst may be arranged, for example, in a mixed bed and stacked bed configuration relative to one another. In the stacked bed configuration it is preferred that the naphthene ring isomerizing catalyst occupy the upstream, or lead, position, while the naphthene ring opening catalyst occupies the downstream, or tail, position. A stacked bed where naphthene ring opening catalyst occupies the lead position can be used, but is less desirable when fewer stacked layers are used. In either the stacked or mixed bed configuration the catalyst charge is desirably distributed in such a manner that the bed is rich in the naphthene ring isomerizing component and lean in the naphthene ring opening component. In a preferred embodiment, the weight ratio of the isomerization component to the ring opening component, based on the total weight of the catalyst bed, may range from about 50 to about 99 parts by weight of the isomerization component and about 50 to about 1 parts by weight of the ring opening component, preferably about 50 to about 95 parts by weight of the isomerization component and about 50 to about 5 parts by weight of the ring opening component, and more preferably about 50 to about 90 parts by weight of the isomerization component and about 50 to about 10 parts by weight of the ring opening component.

In some embodiments it may be desirable to minimize the Ir content of the catalyst system; it is, therefore, desirable that the Ir loadings of the Ir component be drawn from the lower end of the preferred ranges. Pt, Pd, and Pd—Pt loadings for the isomerization component may be drawn from the high end of the preferred ranges. Representative, but not limiting Ir loadings may fall in the range from about 0.01 to about 0.5 wt. %; for Pt and Pd these values may range from about 0.1 to about 2.0 wt. %.

The metals (i.e., Pt, Pd or Ir) of either the isomerizing or ring opening catalyst may be supported on conventional refractory supports. Particularly desirable supports are refractory inorganic oxides. Non-limiting examples of refractory inorganic oxides include alumina, silica, zirconia, titania, chromia, zinc oxide, magnesia, thoria, boria, silica-alumina, silica-magnesia, chromia-alumina, alumina-boria, silica-zirconia, and combinations thereof. Low acidity supports such as alumina are preferred.

In a particularly desirable embodiment, an alumina support is prepared by digesting high purity alumina hydrate powder in a weak organic acid, thereby forming an alumina sol which is then spray-dried by a conventional spray-drying technique to produce the alumina hydrate powder. If the alumina hydrate powder is not of appropriate particle size, it can be ground by any conventional grinding means for reducing the particle size of refractory powders. The alumina hydrate powder is then blended with an effective amount of water, or sol, to form a paste of sufficient consistency for extrusion. The alumina paste is then extruded into an appropriate shape, such as pellets, dried and calcined at temperatures from about 400° C. to about 650° C. The metals can be introduced in any one or more of the above process steps. A more complete description of this process is described in U.S. Pat. No. 5,015,614, which is incorporated herein by reference.

In one embodiment, the metals of the ring opening catalyst can be supported on a modified refractory substrate. The modified refractory substrate may be prepared by incorporating therein an effective amount of modifier. The modifier is such that, when used in an effective amount, it contributes to the resulting ring opening catalyst an improved overall selectivity with respect to linear paraffin functionality when compared to an identical catalyst not containing such modifiers. The term "effective amount of modifier" as used herein refers to the concentration range of modifier which, when used in a ring opening process, will improve the selectivity to linear paraffin functionality of the ring opened product.

Preferred elements that can be incorporated as modifiers into the substrate of the ring opening catalyst for the purposes of this invention include Cs, Mg, Ca, and Ba. Ca, Mg, and Ba are more preferred, with Mg being most preferred.

Generally, the modifier concentration will be at least from about 0.1 to about 50 wt. %. Preferably, the modifier concentration will be about 0.5 to about 40 wt. %, more preferably from about 1 to about 30 wt. %, and most preferably from about 2 to about 25 wt. %. The modifier component can be incorporated into the substrate during any stage of production.

The modifier elements are preferably added to the substrate material as aqueous solutions of their common salts, preferably nitrates, nitrites, oxides, hydroxides, halides, carboxylates, and the like using either incipient wetness or absorption from solution techniques. Incipient wetness is a preferred procedure. Although the modifier can be added to the substrate material after extrusion of the substrate, it is preferable to add modifier prior to extrusion to ensure homogeneity of the modifier elements throughout the substrate.

The modified substrate compositions of this invention are also characterized as having: (i) a surface area greater than about 50 $m^2/g$, preferably from about 100 to about 700 $m^2/g$, and more preferably from about 100 to about 300 $m^2/g$; (ii) a bulk density from about 0.3 to about 1 g/ml, preferably from about 0.4 to about 0.8 g/ml; (iii) an average pore volume from about 0.2 to 1.1 ml/g, preferably from about 0.3 to about 0.8 ml/g; and (iv) an average pore diameter from about 30 to about 300 Angstroms.

The metals may be added to the refractory support by conventional techniques. Preferred techniques include incipient wetness impregnation and absorption from excess aqueous solution. Alternatively, the metals may be incorporated into the support material during its preparation as disclosed and claimed in U.S. Pat. No. 4,963,249, the description of which is incorporated herein by reference.

The metals may also be added to the substrate in precursor form. Suitable metal precursors are the halides, the halometallic acids, nitrates, nitrites, amine halo complexes, amine nitrate complexes, and amine nitrite complexes. Metal deposition from organic solvents may also be practiced using organometallic complexes such acetylacetonates, carbonyls and the like. Decomposition of the deposited complexes may be accomplished thermally in an air, hydrogen, or inert atmosphere by conventional heating, or by the application of microwave or ultrasonic radiation.

In an alternative embodiment, the linear paraffin functionality of the ring opened product can be improved by adding to the ring opening, Ir-containing catalyst at least one other or "second" Group VIII metal selected from Pt, Ru, Rh in an amount effective for opening a naphthene ring-containing compound at a tertiary carbon site. The combination of the Ir and the second Group VIII metal is particularly effective in ring opening a naphthene ring at a tertiary carbon site. This means that a product having a relatively high degree of linear paraffin functionality can be formed.

As defined herein, a tertiary carbon (3° carbon) is the site of location of a substituent group on a naphthene ring compound. Tertiary carbons are represented by such structural features, for example, as —CH(R)—CH$_2$—and CH(R)—CH(R)— where R is a carbon-containing chain, preferably a $C_1$–$C_{10}$ carbon-containing chain.

In ring opening at a tertiary carbon site, it is preferred that the ring opening, Ir-containing catalyst additionally comprise at least one of Pt, Ru, and Rh. Pt is particularly preferred. The Ir content of these catalysts may range from about 0.1 to about 2 wt. %, preferably about 0.3 to about 1.5 wt. %, more preferably about 0.5 to about 1.2 wt. %, and most preferably about 0.5 to about 1.0 wt. %. The content of the second Group VIII metal in a bimetallic composition may range from about 0.001 to about 2.0 wt. %, preferably about 0.005 to about 1.5 wt. %, more preferably about 0.007 to about 1.3 wt. %, and most preferably about 0.01 to about 1 wt. %. Preferred catalyst compositions (wt. %) include 0.01 Me-0.9 Ir, 0.05Me-0.9 Ir, 0.1 Me-0.9 Ir, 0.3 Me-0.9 Ir, and 0.6 Me-0.9 Ir where Me is at least one of Pt, Rh, and Ru.

The catalysts employed may be activated according to conventional methods. For example, they may be activated by drying in air at a temperature ranging from about ambient temperature to about 300° C. for about 4 to about 24 hours and reducing in-flowing hydrogen, preferably in situ, at a temperature ranging from about 200° C. to about 600° C. for about 0.5 to about 24 hours. Drying at temperatures below 200° C. and reducing from about 350 to about 500° C. for about 4 hours are preferred.

Feedstreams employed with the catalyst system will typically contain a mix of hydrocarbons having one or more of the naphthene ring-containing compositions, and the naphthene ring-containing compositions preferably contain at least one alkyl substituent. Preferably, the feedstream will comprise at least 5 wt. % of at least one naphthenic ring-containing compound, more preferably at least 25 wt. %, most preferably at least 50 wt. %. Typically the feedstream will comprise from about 5 to about 85 wt. % of at least one naphthenic ring-containing compound.

As used herein, a naphthene or a naphthenic ring-containing composition refers to a cycloalkane or a composition containing at least one cycloalkane ring in its structure. For example, the term can refer to either a $C_5$ or $C_6$ ring-membered cycloparaffin. The cycloparaffin can also include various side chains, particularly one or more alkyl side chains of 1–10 carbons. In addition the cycloparaffin can be attached or fused to other ring structures, forming two or three membered ring compounds. The additional ring members can be saturated or unsaturated, as long as at least one ring of the complete structure contains a tertiary carbon. Examples of two and three membered ring structures that can contain a tertiary carbon include saturated or partially saturated naphthalenes, indenes, fluorenes, phenanthrenes, anthracenes, acenaphthalenes, and biphenylenes.

A feedstream which is to be ring opened will typically contain a mix of hydrocarbons having one or more of the naphthene ring-containing compositions, and the naphthene ring-containing compositions preferably contain at least one alkyl substituent. Preferably, the feedstream will comprise at least 5 vol. % of at least one naphthenic ring-containing compound more preferably at least 25 wt. %, most preferably at least 50 wt. %. Typically the feedstream will comprise from about 5 to about 85 vol. % of at least one naphthenic ring-containing compound.

In a more preferred embodiment, the hydrocarbon containing the naphthene ring compositions that are to be opened will include $C_5$ and $C_6$ naphthene ring compounds that do not include additional ring members. Non-limiting examples of these compounds include methylcyclopentanes, ethylcyclopentanes, propylcyclopentanes, butylcyclopentanes, pentylcyclopentanes, methylcyclohexanes, ethylcyclohexanes, propylcyclohexanes, butylcyclohexanes, and pentylcyclohexanes. Preferably; the $C_5$ and $C_6$ ring naphthene ring compounds contain alkyl substituents.

Naphthenic ring-containing compounds are found in a wide variety of hydrocarbon feeds, such as petroleum streams boiling in the distillate range. These streams will typically include a variety of chemical compounds, including multi-ring compositions. Preferably, this invention uses a petroleum feed stream, which has a boiling point of from about 175° C. to about 600° C. Examples of such a feed stream include diesel fuel, jet fuel, heating oil, gas oil, and light cycle oil. Gas oil includes vacuum gas oil boiling in the range of from about 340° C. to about 565° C., which is typically derived from vacuum distillation of crude oil, or it can be obtained by conversion of products such as coker gas oil or heavy cat cycle oil. Other feed streams can also be used if appropriately pre-treated. These streams include chemical feed streams and lube streams.

To convert naphthene compounds to paraffins, the catalysts of this invention are contacted with an appropriate feed stream under catalytic ring opening conditions. Preferred conditions are such that the $C_5$ and $C_6$ rings of the naphthene compounds are opened when contacted with the catalyst. Suitable process conditions include a temperature ranging from about 150° C. to about 500° C., preferably from about 400° C. to about 450°, a total pressure ranging from about 100 to about 3,000 psig, preferably from about 100 to about 2,200 psig, more preferably about 100 to about 1,500 psig, a liquid hourly space velocity ranging from about 0.1 to about 10 V/V/Hr, preferably from about 0.5 to about 5 V/V/Hr, and a hydrogen treat gas rate ranging from about 200 to about 10,000 SCF/B, preferably from about 500 to about 5000 SCF/B. SCF/B means standard cubic feet per barrel, and V/V/Hr means volume of feed per volume of catalyst per hour.

It is preferred that the process be operated at the higher end of the temperature ranges. At the higher end of the temperature ranges, the isomerization catalyst has an increased selectivity to isomerize $C_6$ naphthene ring-containing compounds to the more easy to ring open $C_5$ naphthene ring-containing compounds. The Ir-containing catalyst can then more easily ring open the $C_5$ naphthene ring containing compounds. However, while increased process temperatures are generally desirable, such increased temperatures may also result in the formation of light, saturated products such as methane. Accordingly, the process temperature should be regulated to provide for increased isomerization selectivity without forming a substantial amount of light saturated products.

In order to further moderate or suppress undesirable methane formation, a hydrogenolysis suppressor (i.e., cracking suppressor) such as one or more Group IB, IIB, and IVA metals may be incorporated into either the naphthene ring isomerizing catalyst or the naphthene ring opening catalyst. Preferred Group IB metals include Cu, Ag, and Au. Preferred Group IIB metals include Zn. Preferred Group IVA metals include Sn. These metals can be used alone or in mixtures thereof. Particularly preferred Group IB, IIB and IVA metals are Cu, Sn, or Zn, all of which can be used alone or in mixtures thereof. Sn is most preferred.

The Group IB, IIB or IVA metals may be included in the ring opening catalyst in an amount effective to moderate cracking of a naphthene ring-containing feed to form methane. Desirably, the Group IB, IIB or IVA metals are also present in an amount effective for enhancing ring opening of the naphthene ring-containing compounds which contain a tertiary carbon site. The total loading of the Group IB, IIB or IVA metals can range from about 0.01 to about 5.0 wt. %. Total loadings from about 0.01 to about 3.0 wt. % are preferred, loadings from about 0.01 to about 2.0 wt. % are more preferred, and loadings from about 0.01 to about 1.0 wt. % are most preferred. Preferred, but not limiting, catalyst compositions within these limits include Ir—Cu, Ir—Sn, Pt—Ir—Sn, Pt—Cu, and Pt—Sn.

Conventional catalytic ring opening reactors may be used in the process of this invention. A fixed bed reactor system wherein the feedstock is passed over one or more stationary beds of catalyst is preferred. Multiple reactors can be used in either series or parallel configurations.

Hydrogen gas conducted to the reaction process may flow over the catalyst either in a direction concurrent or countercurrent with the feedstock. Hydrogen is supplied to saturate the carbons where ring opening occurs, and it is preferably supplied in stoichiometric excess. Preferably, reactor effluent is passed to a separation zone where hydrogen that has not been consumed in the reaction process can is separated off and can be recycled to the reaction zone together with make-up hydrogen as needed or cascaded to a lower pressure unit for further processing.

Countercurrent reactors incorporating the catalyst of this invention are a preferred embodiment, since properly constructed countercurrent reactors can provide better contacting of reactants and treat gas and provide better removal of $H_2S$ which may be present. Such a reactor is disclosed in U.S. Pat. No. 5,942,197, the description of which is incorporated herein by reference. This preferred design is less susceptible to flooding than conventional countercurrent reactors because it incorporates passageways to bypass one or more catalyst beds. Bypass of at least a portion of the hydrogen treat gas is designed to occur when the pressure differential across the catalyst bed increases to a predefined threshold correlating to a near-flood condition. When gas bypasses the catalyst bed, the pressure differential across the catalyst bed decreases to permit the downward flow of liquid. When the pressure differential falls below a predefined level, the bypassing of gas is automatically stopped.

It is preferred that the feed streams be hydrotreated prior to ring opening to reduce sulfur content to low levels, preferably less than about 10 ppm, more preferably less than about 1 ppm, most preferably less than about 0.1 ppm. This is particularly desirable when high sulfur feeds are used in the ring opening process, since the ring opening catalysts are sensitive to high sulfur content.

Hydrotreating to reduce sulfur is referred to herein as hydrodesulfurization. Conventional hydrodesulfurization catalysts may be used to reduce the sulfur content of feed containing sulfur compounds to the preferred levels.

Non-limiting examples of conventional hydrodesulfurization catalysts which may be used to reduce the sulfur content of the feed include catalysts which comprise a Group VI metal with one or more Group VIII metals as promoters, the metals being on a refractory support. Conventional hydrodesulfurization processes are conducted at pressures ranging from about 50 to about 2000 psig, preferably from about 100 to about 1500 psig, liquid hourly space velocities ranging from about 0.2 to about 6 V/V/Hr, and a hydrogen gas rate from about 200 to about 5000 SCF/B.

Sulfur sorbents, including regenerable sulfur sorbents, may also be used to reduce the sulfur content of the feed. These materials are capable of removing the easy sulfur compounds, particularly hydrogen sulfide, under relatively mild sulfur removing conditions. Examples of sulfur sorbents include metal oxides. These systems are disclosed in U.S. Pat. No. 5,928,498; 5,925,239; 5,935,420; 4,003,823; U.S. Pat. No. 4,007,109; U.S. Pat. No. 4,087,348; U.S. Pat. No. 4,087,349; U.S. Pat. No. 4,119,528; and U.S. Pat. No. 4,127,470 all of which are incorporated by reference herein.

If significant aromatic compounds are present in the feed stream, it is desirable to saturate them. It is preferred that the feedstock contain less than about 20 wt. % total aromatic compounds, preferably less than about 15 wt. %, more preferably less than about 10 wt. %.

The aromatics saturation (ASAT) process may be performed in one or a series of reactors either before or after the ring opening process, since either mode will generally result in a product having increased cetane number due to the lowering of the aromatic content. Saturation of aromatics in the feed is preferred, however, prior to the ring opening process. This is because saturation of aromatics tends to result in the formation of additional naphthenes, providing additional material that can ultimately be converted using the catalyst of this invention to form compounds having a higher degree of linear paraffin functionality. In another preferred embodiment, a hydrodesulfurization reactor will be placed in front of the aromatics saturation reactor so that the catalyst in the aromatics saturation reactor will contact low sulfur feedstock.

Any conventional aromatic saturation process may be used to hydrogenate the aromatic rings of the aromatic compounds in connection with the invention. Typical conditions for saturating aromatics-containing feedstocks include temperatures from about 150° C. to about 400° C., pressures from about 100 to about 2000 psig, space velocities from about 0.4 to about 6 V/V/Hr, and hydrogen gas rates from about 200 to about 6000 standard cubic feet per barrel (SCF/B). Lower temperatures are found to be most desirable for the hydrogenation or saturation reactions since nonselective cracking reactions thereby are minimized. Selective saturation of the aromatics results in a saturated intermediate from the hydrogenation zone usually containing less than 15 weight % total aromatics.

Ring opening may also be practiced in a variety of stacked or mixed bed configurations along with aromatics saturation and sulfur removal. The stacked and mixed beds may occupy a single reactor or multiple reactors, and may take place in either co-current or countercurrent mode. The stacking of fixed beds of catalyst refers to the sequence of beds disposed with respect to the direction of flow of the liquid phase reactants. In a single reactor, such beds would be vertically disposed from top to bottom. In a series of reaction vessels the sequence is defined by the flow of the liquid phase.

A reactor may, for example, be loaded to have stacked layers of a sulfur reducing catalyst (e.g., a hydrodesulfurization (HDS) catalyst); a sulfur sorbent (sorbent); an aromatics saturation (ASAT) catalyst; and/or a ring opening (RO) catalyst. Specific examples of stacked catalyst arrangements include:

HDS/ASAT/sorbent/RO; HDS/RO/ASAT; sorbent/ ASAT/RO; and

HDS/sorbent/ASAT/RO. Preferred mixed bed catalyst arrangements include: RO+ASAT; sorbent+RO; sorbent+ASAT+RO; and sorbent+HDS+RO. Conditions favoring the ring opening function are preferred.

The ring opened product may be recovered after the final processing step, i.e., after ring opening, after an optional ASAT final step, or after any further optional treatment step, according to conventional methods. The recovered product may be used directly, for example, as a diesel fuel, jet fuel, gas oil, and heating oil, and it may be blended with other petroleum products and used as a diesel fuel, jet fuel, gas oil, and heating oil. When blended, it is preferred that the ring opened product be blended with a petroleum stream having a boiling point ranging from about 175° C. to about 600° C., wherein the blend has a cetane number of at least about 40.

The Periodic Table of the Elements referred to herein appears on the inside cover page of the Merck Index, 12th Ed., Merck & Co., 1996.

This invention will be better understood with reference to the following examples, which are intended to illustrate specific embodiments within the overall scope of the invention as claimed.

EXAMPLES

Metal loadings are in weight percent, based on the weight of the catalyst. For example, a catalyst of 0.9 wt. % Ir and 0.9 wt. % Pt, based on the weight of the catalyst is written as 0.9 Ir-0.9 Pt.

Example 1

A 0.9 wt. % Pt catalyst was prepared by impregnating 50 g of reforming grade alumina with a chloroplatinic acid stock solution (28 mg/ml Pt). The catalyst was dried at 120° C. for 24 hr and reduced at 450° C. for 3 hr. The catalyst was used to ring open methylcyclohexane, and the results are shown in Table 1.

Example 2

A 0.9 wt. % Pd catalyst was prepared by impregnating 50 g of reforming grade alumina with a palladium chloride stock solution (50 mg/ml Pd). The catalyst was dried at 120° C. for 24 hr and reduced at 450° C. for 3 hr. The catalyst was used to ring open methylcyclohexane, and the results are shown in Table 1.

Example 3

A 0.9 wt. % Ir catalyst was prepared by impregnating 50 g of reforming grade alumina with a chloroiridic acid solution (16 mg/ml Ir). The catalyst was dried a 120° C. for 24 hr and reduced at 450° C. for 3 hr. The catalyst was used to ring open methylcyclohexane, and the results are shown in Table 1.

TABLE 1

Ring Opening Methylcyclohexane Over 0.9 Pt, 0.9 Pd, And 0.9 Ir Catalysts (350° C.; 800 psig; 1 W/H/W For Pt, Pd; 10 W/H/W For Ir, $H_2$/Oil = 6)

| Example | Catalyst | Conversion, Wt. % | Paraffin Yield, Wt. % | $C_7$ Cyclopentanes, Wt. % |
|---------|----------|-------------------|----------------------|---------------------------|
| 1 | 0.9 Pt | 25 | 5 | 19 |
| 2 | 0.9 Pd | 47 | 13 | 34 |
| 3 | 0.9 Ir | 45 | 32 | 0 |

Examples 1–3 demonstrate the ineffectiveness of Pt and Pd as ring opening metals relative to Ir as measured by the conversion of methylcyclohexane to paraffins despite a tenfold difference in space velocities. Pt and Pd are shown to be effective isomerization catalysts as the isomerization of the methylcyclohexane to $C_7$ cyclopentanes is significant over both catalysts as about 70% of the conversion is to isomerized product.

In the following examples utilizing mixed and stacked beds the catalysts are selected from those found in Examples 1–2 and 4. The beds were comprised of 6 parts of Ir catalyst, 94 parts of Pt and/or Pd catalyst, or 94 parts of reformer grade alumina.

Example 4

A 0.1 wt. % Ir catalyst was prepared by impregnating 50 g of reforming grade alumina with a chloroiridic acid stock solution (16 mg/ml Ir). The catalyst was dried at 120° C. for 24 hr and reduced at 450° C. for 3 hr. The catalyst was used in Examples 5–10.

Example 5

The catalyst of Example 4 was admixed with alumina and used to ring open methylcyclohexane. The results are shown in Table 2.

Example 6

The catalyst of Example 4 was layered with alumina and used to ring open methylcyclohexane. The Ir catalyst occupied the lower region of the bed. The results are shown in Table 2.

Example 7

The catalyst of Example 4 was admixed with the Pt catalyst of Example 1 and used to ring open methylcyclohexane. The results are shown in Table 2.

Example 8

The catalyst of Example 4 was layered with the Pt catalyst of Example 1 and used to ring open methylcyclohexane. The Ir catalyst occupied the lower region of the bed. The results are shown in Table 2.

Example 9

The catalyst of Example 4 was admixed with the Pd catalyst of Example 2 and used to ring open methylcyclohexane. The results are shown in Table 2.

Example 10

The catalyst of Example 4 was layered with the Pd catalyst of Example 2 and used to ring open methylcyclohexane. The Ir catalyst occupied the lower region of the bed. The results are shown in Table 2.

TABLE 2

Ring Opening Methylcyclohexane Over Ir, Pt/Ir, and Pd/Ir Catalyst Beds (350° C., 800 psig, 1 W/H/W, $H_2$/Oil = 6)

| Example | Catalyst | Type | Conversion, Wt. % | Paraffin Yield, Wt. % | $C_7$ Cyclopentanes, Wt. % |
|---|---|---|---|---|---|
| 5 | Ir | Mixed | 24 | 20 | 0 |
| 6 | Ir | Stack | 49 | 38 | 0 |
| 7 | Pt/Ir | Mixed | 70 | 56 | 2 |
| 8 | Pt/Ir | Stack | 64 | 54 | 1 |
| 9 | Pd/Ir | Mixed | 63 | 52 | 3 |
| 10 | Pd/Ir | Stack | 72 | 62 | 1 |

Examples 7–10 demonstrate that the mixed and stacked dual catalyst arrangements of this invention are superior to Ir only, all systems containing the identical amount of Ir catalyst. Comparison of Examples 7–10 with Examples 1–2 and with Examples 5–6 illustrates that the dual catalyst systems outperform their individual components and that there exists a synergy in the dual catalyst arrays that is absent in the individual cases. The small quantities of surviving cyclopentanes in Examples 7–10 relative to Examples 1–2 indicate the source of this synergy is the combination of ring isomerization catalyzed over Pt and/or Pd with the ring opening efficiency of Ir for converting cyclopentane rings.

Example 11

A 0.9 Pt-0.1Ir catalyst was prepared using the chloroplatinic and chloroiridic acid stock solutions of Examples 1 and 3 and reforming grade alumina. The catalyst was pretreated and tested as in Example 1. Table 3 presents the results for ring opening methylcyclohexane.

Example 12

A 0.9 Pd-0.1Ir catalyst was prepared using the palladium chloride and chloroiridic acid stock solutions identified in Examples 2 and 3 and reforming grade alumina. The catalyst was pretreated and tested as in Example 2. Table 3 presents the results for ring opening methylcyclohexane.

TABLE 3

Ring Opening Methylcyclohexane Over Pt-Ir And Pd-Ir Catalysts (350° C., 800 psig, 1 W/H/W, $H_2$/Oil= 6)

| Example | Catalyst | Conversion, Wt. % | Paraffin Yield Wt. % | $C_7$ Cyclopentanes Wt. % |
|---|---|---|---|---|
| 11 | Pt-Ir | 36 | 32 | 0 |
| 12 | Pd-Ir | 60 | 26 | 27 |

Comparison of Examples 11 and 12 with Examples 7–10 illustrates that the synergy observed in the latter cases is absent when both metals occupy a common support. In Examples 11 and 12 the Ir loading in the catalyst bed exceeds by greater than an order of magnitude that present in Examples 7–10. On the basis of improved Ir utilization and efficiency the catalyst combinations of Examples 7–10 are preferred.

Preparation of Saturated Cyclic Feedstock A

An aromatics solvent stream containing primarily $C_{11}$, and $C_{12}$ naphthalenes with an API gravity of 10 was hydrogenated over 180 g (250 cc) of a 0.6 wt. % Pt on alumina catalyst. The catalyst was prereduced in flowing hydrogen at 750° F. for 16 hr at atmospheric pressure. The aromatics solvent feedstock was passed over the catalyst at 1800 psig, 550° F., 1 LHSV, 7000 SCF/B hydrogen treat gas rate. The saturated product had an API gravity of 31.6 and contained less than 0.1 wt. % aromatics and greater than 99 wt. % naphthenes.

Example 13

A reactor was charged with the 0.9 wt. % Ir catalyst of Example 3. Saturated cyclic feedstock A was processed over the Ir catalyst at 600° F., 650 psig, 3000 SCF/B $H_2$, 0.5 LHSV. Key results from this run are summarized in Table 4.

Example 14

A 2 wt. % Pd on alumnina catalyst was prepared by the procedure of Example 2. The catalyst was dried at 120° C. for 24 hours and calcined in air at 500° C. for 3 hours.

A reactor was charged with a stacked bed of 2 wt. % Pd on alumina as the upstream, or top, layer, and 0.9 wt. % Ir on alumina as the downstream, or bottom, layer. The catalysts were charged in a 50/50 ratio by volume. Saturated cyclic feedstock A was processed over the stacked Pd/Ir catalyst at 600° F., 650 psig, 3000 SCF/B $H_2$, 0.5 LHSV. Key results from this run are summarized in Table 4.

TABLE 4

Ring Opening Of Saturated Cyclic Feedstock A Over 0.9 Ir and 2.0 Pd/0.9 Ir Catalysts

| Catalyst | Feed | 0.9 Ir | Stacked Pd/Ir |
|---|---|---|---|
| $C_6^-$ Gas, wt. % | — | 0.7 | 04 |
| Total Liquid Product, wt. % | 100 | 97.2 | 98.5 |
| 375° F.+ Yield, wt. % | 89.0 | 85.3 | 87.0 |
| Total Liquid Product API | 31.6 | 33.7 | 33.4 |
| Paraffins, wt. % | 0.9 | 1.5 | 1.5 |
| One Ring Naphthenes, wt. % | 18.3 | 25.6 | 22.2 |
| Two Ring Naphthenes, wt. % | 80.9 | 72.9 | 76.3 |
| Ring Disappearance, mol. % | — | 6.6 | 3.8 |

The wt. % yield of total liquid product and of 375° F. distillate is higher over the catalyst of this invention due to incrementally lower gas make. The volumetric yield of the Pd/Ir catalyst is favored by the higher liquid and distillate yields at equivalent API. While the ring disappearance at these conditions is lower over the Pd/Ir catalyst, the relative distillate yields and ring disappearance values illustrate higher selectivity for the stacked Pd/Ir catalyst.

Having now fully described this invention, it will be appreciated by those skilled in the art that the invention can be performed within a wide range of parameters within what is claimed, without departing from the spirit and scope of the invention.

What is claimed is:
1. A naphthene ring opening catalyst system comprising:
   (a) a naphthene ring isomerizing catalyst containing a catalytically active naphthene ring isomerization metal supported on a first catalyst support in an amount effective to isomerize a $C_6$ naphthene ring-containing compound to a $C_5$ naphthene ring-containing compound; and (b) a naphthene ring opening catalyst comprising Ir supported on a second catalyst support in an amount effective to ring open a naphthene ring-containing compound wherein said second catalyst support further contains an effective amount of at least one modifier selected from Cs, Mg, Ca, and Ba.

2. The naphthene ring opening catalyst system of claim 1, wherein the isomerizing catalyst and the ring opening catalyst are mixed together.

3. The naphthene ring opening catalyst system of claim 1, wherein the isomerizing catalyst and the ring opening catalyst are in a stacked bed arrangement.

4. The naphthene ring opening catalyst system of claim 1, wherein said catalytically active isomerization metal is at least one of Pt and Pd present in an amount from about 0.1 to about 2.0 wt. %, and wherein said Ir supported on said second catalyst support is present in an amount from about 0.1 to about 2.0 wt. %, based on the weight of the catalyst.

5. The naphthene ring opening catalyst system of claim 4 wherein the naphthene ring opening catalyst contains at least one other Group VIII metal selected from Pt, Rh, Ru present in a range from about 0.001 to about 2.0 wt. %, based on the weight of the catalyst.

6. The naphthene ring opening catalyst system of claim 5, wherein catalytically active isomerization metal and the catalytically active ring opening metal are present at a weight ratio of about 50 to about 99 parts of catalytically active isomerization metal to about 50 to about 1 parts catalytically active ring opening metal, based on the total weight of the catalyst system.

7. The naphthene ring opening catalyst system of claim 1, wherein the first and second supports independently contain at least one refractory inorganic oxide selected from alumina, silica, zirconia, titania, chromia, zinc oxide, magnesia, thoria, boria, silica-alumina, silica-magnesia, chromia-alumina, alumina-boria, silica-zirconia.

8. The naphthene ring opening catalyst system of claim 7, wherein the first and second supports contain alumina.

9. The naphthene ring opening catalyst system of claim 1, wherein at least one of the naphthene ring isomerizing catalyst and the naphthene ring opening catalyst further contains at least one hydrogenolysis suppressor selected from Cu, Ag, Au, Zn, and Sn.

10. The naphthene ring opening catalyst system of claim 9, wherein the hydrogenolysis suppressor is Sn.

11. The naphthene ring opening catalyst system of claim 1, wherein the modifier is Mg.

12. The naphthene ring opening catalyst system of claim 1, wherein the naphthene ring opening catalyst further contains at least one other Group VIII metal selected from Pt, Ru, and Rh in an amount effective for opening a naphthene ring-containing compound at a tertiary site.

13. The naphthene ring opening catalyst system of claim 12, wherein the other Group VIII metal is Pt and is present at a range from about 0.001 to about 2.0 wt. %, based on the weight of the catalyst.

14. A process for opening naphthene rings of naphthene ring-containing compounds in a feed stream, comprising:

providing a naphthene ring-containing feed stream; and contacting the naphthene ring-containing feed stream with a naphthene ring opening catalyst system comprising: (a) a naphthene ring isomerizing catalyst containing a catalytically active naphthene ring isomerization metal supported on a first catalyst support in an amount effective to isomerize a $C_6$ naphthene ring-containing compound to a $C_5$ naphthene ring-containing compound; and (b) a naphthene ring opening catalyst comprising Ir supported on a second catalyst support in an amount effective to ring open a naphthene ring-containing compound wherein said second catalyst support further contains an effective amount of at least one modifier selected from Cs, Mg, Ca, and Ba.

15. The process of claim 14, wherein the isomerizing catalyst and the ring opening catalyst are mixed together.

16. The process of claim 14, wherein the isomerizing catalyst and the ring opening catalyst are in a stacked bed arrangement.

17. The naphthene ring opening catalyst system of claim 16, wherein said catalytically active isomerization metal is at least one of Pt and Pd present in an amount from about 0.1 to about 2.0 wt. %, and wherein said Ir supported on said second catalyst support is present in an amount from about 0.1 to about 2.0 wt. %, based on the weight of the catalyst.

18. The process of claim 17 wherein the naphthene ring opening catalyst contains at least one other Group VIII metal selected from Pt, Rh, Ru present in a range of about 0.001 to about 2.0 wt. %, based on the weight of the catalyst.

19. The process of claim 18, wherein catalytically active isomerization metal and the catalytically active ring opening metal are present at a weight ratio of about 50 to about 99 parts of catalytically active isomerization metal to about 50 to about 1 parts catalytically active ring opening metal, based on the total weight of the catalyst system.

20. The process of claim 14, wherein the first and second supports independently contain at least one refractory inorganic oxide selected from alumina, silica, zirconia, titania, chromia, zinc oxide, magnesia, thoria, boria, silica-alumina, silica-magnesia, chromia-alumina, alumina-boria, silica-zirconia.

21. The process of claim 20, wherein the first and second supports contain alumina.

22. The process of claim 14, wherein at least one of the naphthene ring isomerizing catalyst and the naphthene ring opening catalyst further contains at least hydrogenolysis suppressor selected from Cu, Ag, Au, Zn, and Sn.

23. The process of claim 22, wherein the hydrogenolysis suppressor is Sn.

24. The process of claim 14, wherein the modifier is Mg.

25. The process of claim 14, wherein the naphthene ring opening catalyst further contains at least one other Group VIII metal selected from Pt, Ru, Rh in an amount effective for opening a naphthene ring-containing compound at a tertiary site.

26. The process of claim 25, wherein the other Group VIII metal is Pt and is present at a range of about 0.001 to about 2.0 wt. %, based on the weight of the catalyst.

27. The process of claim 14, wherein ring opening is carried out at a temperature of from about 150° C. to about 400° C., a total pressure from about 100 to about 3,000 psig, a liquid hourly space velocity of about 0.1 to about 10 V/V/Hr, a hydrogen treat gas rate from about 200 to about 10,000 SCF/B, and wherein the feed stream is a petroleum feed stream which has a boiling point of from about 175° C. to about 600° C.

28. The process of claim 27, further comprising ring opening at the tertiary carbon site, thereby forming a ring opened product having increased linear paraffin functionality relative to that of the feed stream.

29. The process of claim 28, further comprising recovering the ring opened product.

30. The process of claim 29, further comprising blending the ring opened product with a petroleum stream having a boiling point from about 175° C. to about 600° C., wherein the blend has a cetane number of at least 40.

* * * * *